United States Patent [19]

Aslanian

[11] Patent Number: 5,113,904

[45] Date of Patent: * May 19, 1992

[54] FLOW CONTROL DEVICE FOR ADMINISTRATION OF INTRAVENOUS FLUIDS

[76] Inventor: Jerry L. Aslanian, 6210 N. Camelback Manor Dr., Paradise Valley, Ariz. 85253

[ * ] Notice: The portion of the term of this patent subsequent to Feb. 7, 2006 has been disclaimed.

[21] Appl. No.: 639,830

[22] Filed: Jan. 9, 1991

Related U.S. Application Data

[63] Continuation of Ser. No. 305,078, Feb. 2, 1989, Pat. No. 5,005,604, which is a continuation of Ser. No. 630,632, Jul. 13, 1984, abandoned.

[51] Int. Cl.$^5$ .................. F16K 5/10; F16K 37/00
[52] U.S. Cl. ...................... 137/556; 251/209; 251/312; 604/246; 604/248
[58] Field of Search ............... 137/556; 251/208, 209, 251/309, 311, 312, 314; 604/32, 246, 248

[56] References Cited

U.S. PATENT DOCUMENTS

| | | | |
|---|---|---|---|
| 2,505,124 | 4/1950 | Lepeschkin | 137/556 X |
| 3,276,472 | 10/1966 | Jinkens et al. | 136/556 |
| 3,305,211 | 2/1967 | Phillips | 251/209 X |
| 3,475,002 | 10/1969 | Phillips | 251/209 X |
| 3,698,683 | 10/1972 | De Angelis | 251/209 |
| 3,788,602 | 1/1974 | Kitzie | 251/312 |
| 4,147,184 | 4/1979 | Jess | 251/312 X |
| 4,802,506 | 2/1989 | Aslanian | 137/556 |

Primary Examiner—John Rivell
Attorney, Agent, or Firm—Gregory J. Nelson

[57] ABSTRACT

A metering apparatus and system for controlling the administration of IV fluids having a valve housing with a valving chamber therein. A rotatable valve body member is positioned within the valve chamber and a valve passageway of variable cross-sectional area is provided at either the chamber or on the valve member. The effective area and length of the valve passageway interposed between the inlet and outlet to the valve is adjustable to regulate flow by moving the valve body relative to the valve member. Various accessories can be selectively attached to the basic valve configuration including a backplate which facilitates single-handed operation and an optional cover plate which may be secured to the backplate to provide security from patient tampering. In a preferred embodiment the valve housing and internal valve members are fabricated from dissimilar plastic materials of different hardness to improve the sealing therebetween.

8 Claims, 5 Drawing Sheets

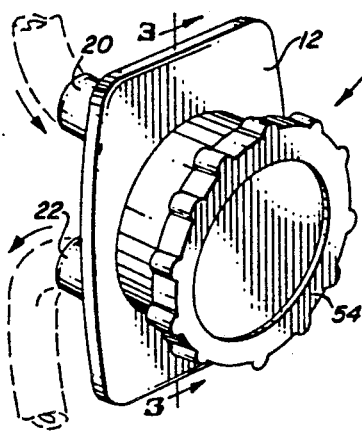
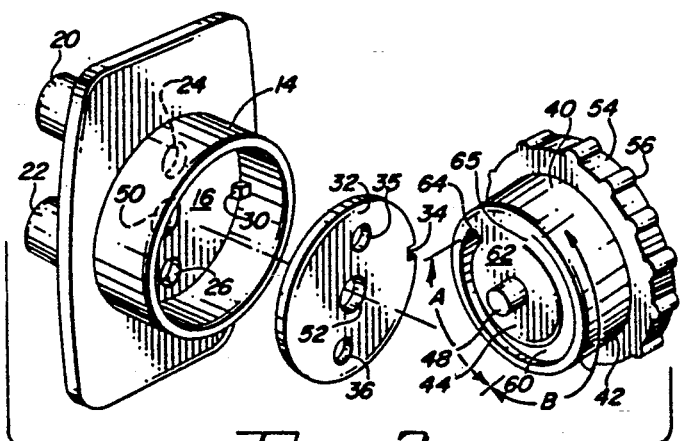
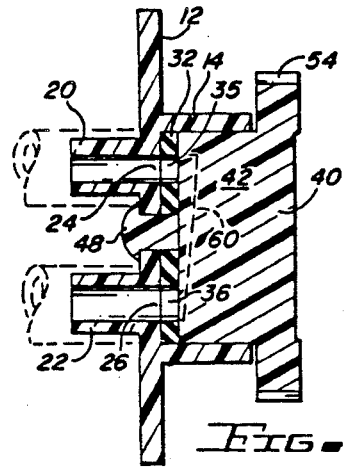
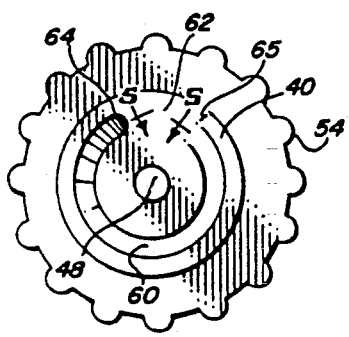
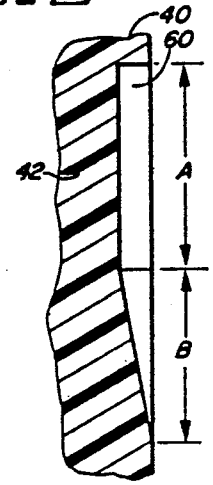
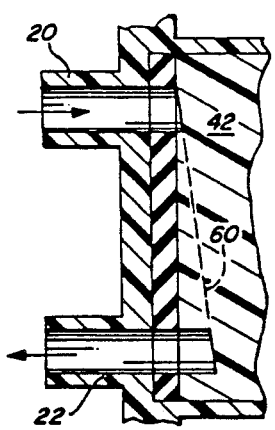
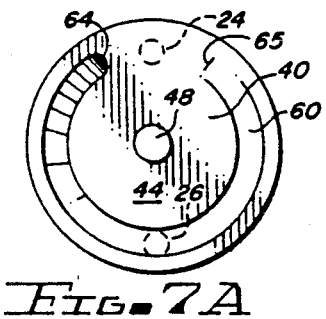
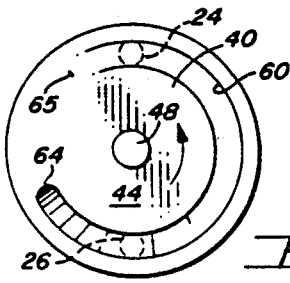
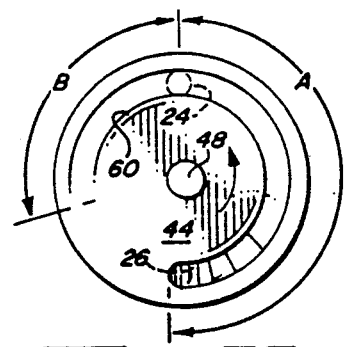

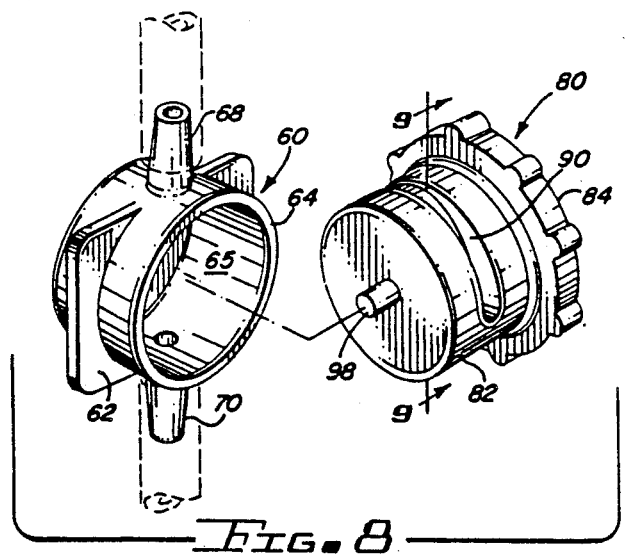
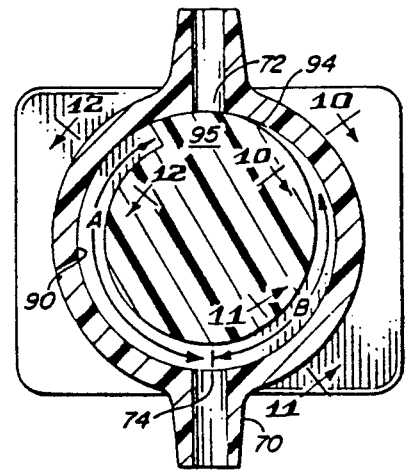
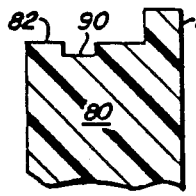
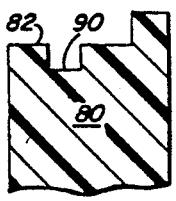
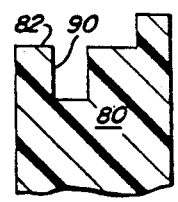
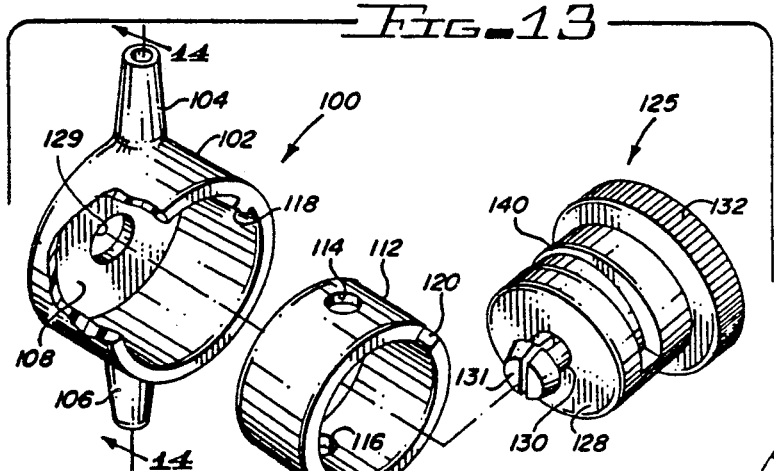
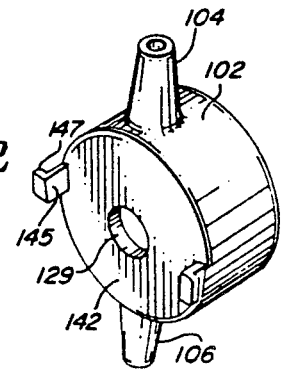
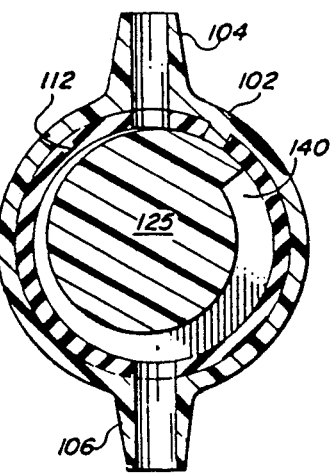
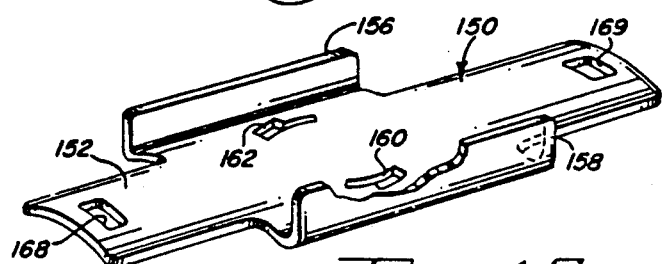

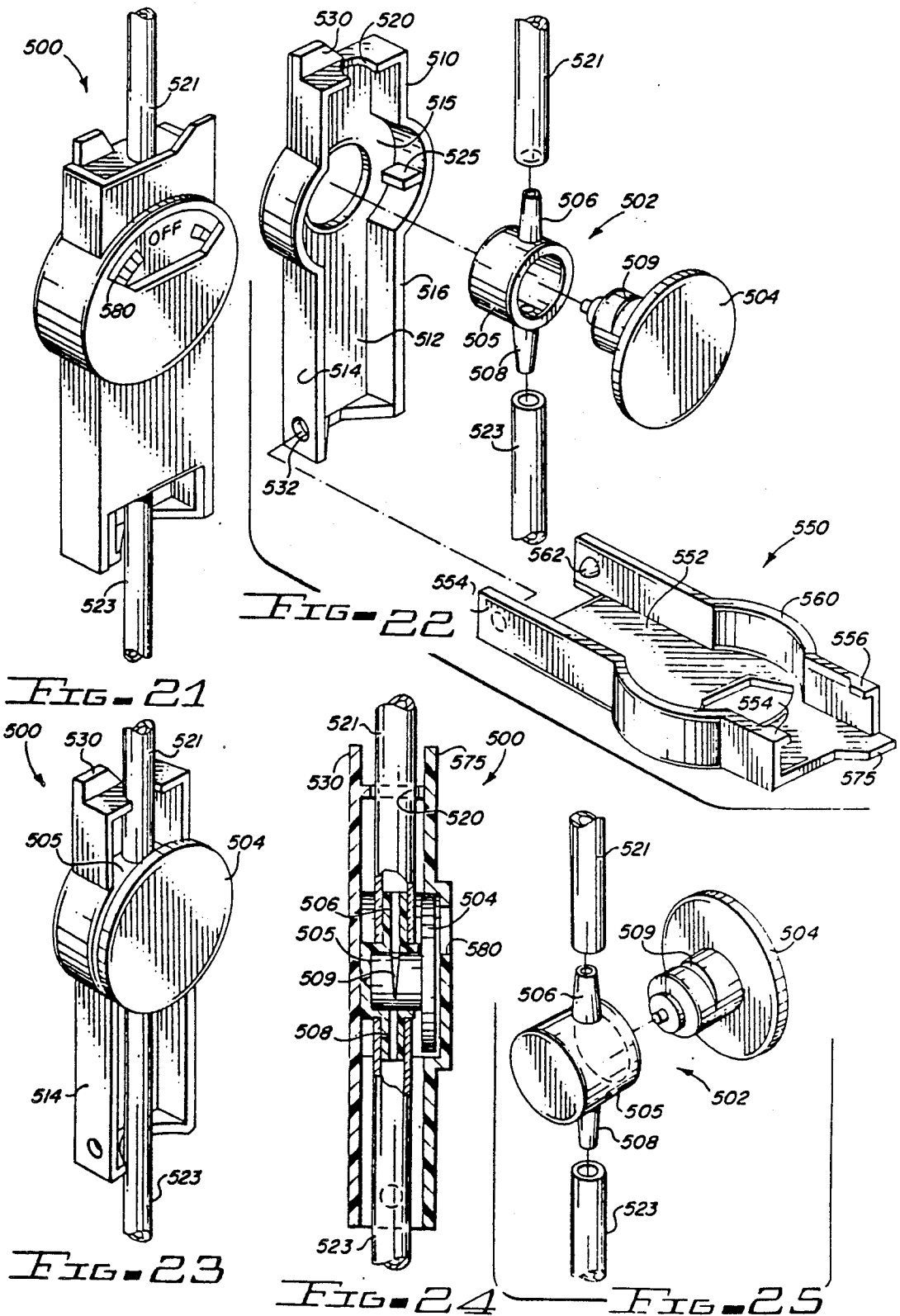

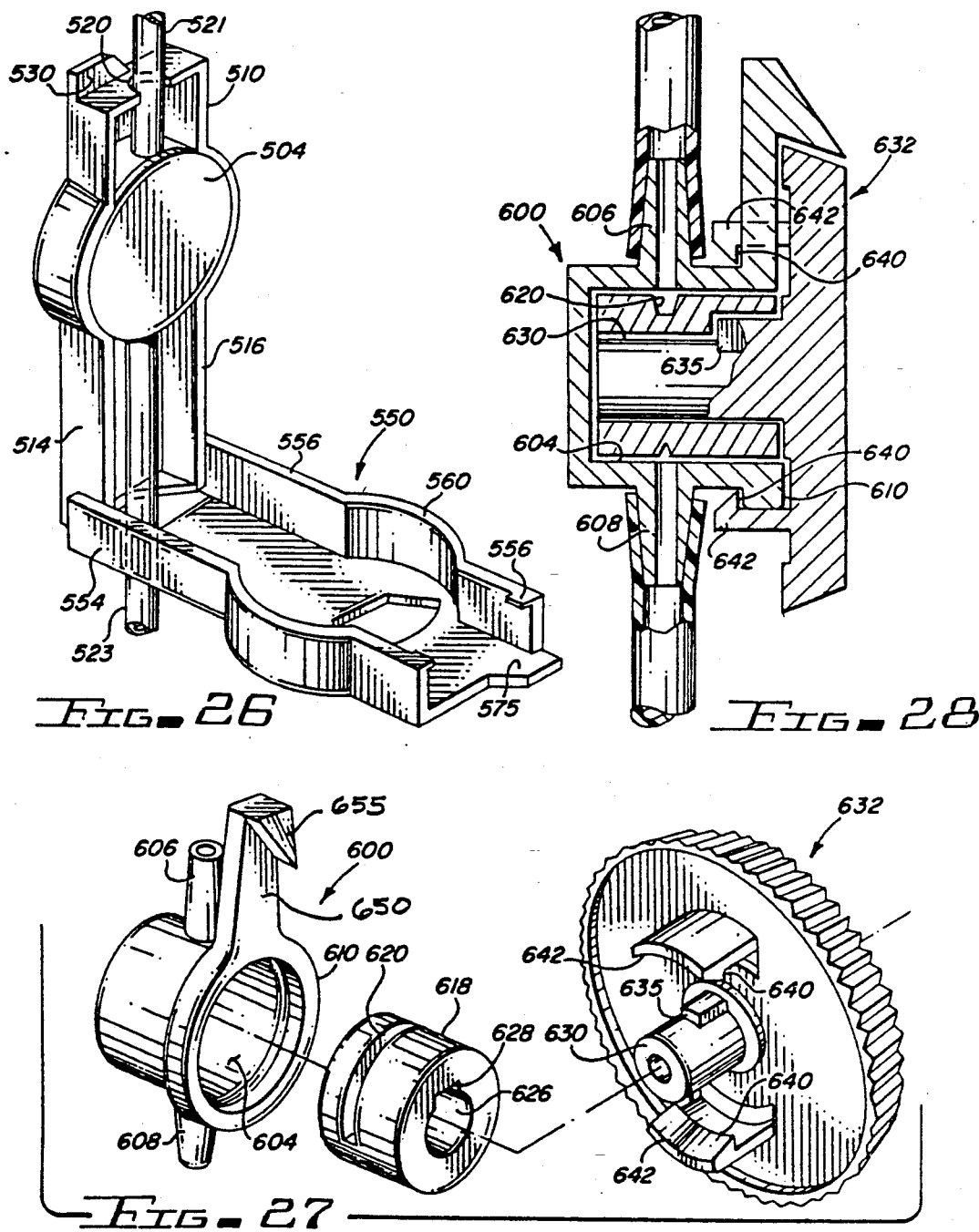

FLOW CONTROL DEVICE FOR ADMINISTRATION OF INTRAVENOUS FLUIDS

This is a continuation of Ser. No. 305,078 filed Feb. 2, 1989 entitled FLOW CONTROL DEVICE FOR ADMINISTRATION OF INTRAVENOUS FLUIDS, now U.S. Pat. No. 5,005,604, which is a continuation of Ser. No. 630,632 filed Jul. 13, 1984 entitled FLOW CONTROL DEVICE FOR ADMINISTRATION OF INTRAVENOUS FLUIDS, now abandoned.

The present invention relates to a device for regulating and controlling the flow of intravenous (IV) and parenteral fluids. More particularly, the present invention relates to a flow metering device for precisely establishing and maintaining a preselected flow rate during the administration of IV liquids to the patient.

The gravity administration of fluids by IV infusion is a common medical procedure. Representative intravenous fluids include blood, plasma, dextrose and isotonic saline solutions. IV infusions are generally carried out with the container of IV fluid suspended above the patient. Customarily such containers have a seal which is broken by the insertion of a spike and the fluid is delivered to the patient at an administration needle through a drip chamber and flexible tubing connected to the spike. The purpose of the drip chamber is to facilitate the determination of the flow or drip rate through the tubing. The infusion rate is generally regulated by use of an external pinch valve or roller clamp associated with the tubing for the more common gravity type infusions.

Initially when infusions are carried out, the tubing and needle are purged of air by initiating a flow of fluid through the tubing. The needle is then inserted into a venapuncture site at a suitable location such as in the forearm or wrist of the patient and infusion of fluid is initiated. Preferably when the venapuncture site occurs in the lower arm of the patient, the arm should be properly stabilized on a contoured IV arm support. Medical personnel administering the IV will adjust the pinch valve or roller to restrict the IV tubing and the number of drops passing through the drip chamber are counted. The appropriate flow rate is established by trial and error, by progressively restricting or opening the tubing at the pinch valve.

The administration procedure described above requires the attention of medical personnel for a substantial time in the initial establishment of the proper flow rate and in continual monitoring. It is the general practice of medical personnel to periodically check the flow rate by counting the drops of fluid that pass through the drip chamber. Conventional procedures as described not only require substantial time but are often inaccurate. Temperature changes cause expansion and contraction of the IV tubing allowing the flow rate to vary. The tubing may lose "memory" and collapse under continuos squeezing necessitating constant readjustment of the setting. Roller clamps or pinch valves of the general type described have a tendency to slip off the tubing which can pose a threat to the patient.

Independent tests have indicated that conventional pinch valves and roller clamps maintain flow only within about 25% accuracy thereby requiring constant readjustment. Accordingly, it will be appreciated that control of infusion rates with an acceptable degree of accuracy using conventional pinch valves and roller clamps is extremely difficult even with constant attention on the part of attending medical personnel.

Various expedients have been resorted to in an effort to correct the problem set forth above. Flow regulating devices of various types have been developed and can be found in the prior art. U.S. Pat. No. 3,785,378 to Stewart shows a valve for the administration of intravenous fluids which has an annular member forming a central passage through which fluid is flowable to an end face having multiple grooves. The inner ends of the multiple grooves communicate with the passage and a flow control member is rotatable to place the flow port successively and selectively in communication with the grooves to vary the flow rate.

Another approach to the problem is found in U.S. Pat. No. 3,877,428 to Seagle et al which patent shows an infusion control device for selectively controlling the rate of administration of fluids to a patient. The control device is attachable along the IV tubing and includes a rotatable metering member defining a capillary flow path between the input and output of the control device. A metering plate is axially rotatable with respect to the input and output ports to vary the effective length of the flow path so as to regulate flow between full flow and zero flow conditions.

A somewhat similar approach is shown in U.S. Pat. No. 3,880,401 which discloses a flow metering valve having inner and outer component parts which are movable relative one to another at screw threads to effect relative axial movement of a metering valve plug with respect to a metering bore for regulating and terminating flow through the valve flow passage.

Prior U.S. Pat. Nos. 4,294,246 and 4,361,147, commonly assigned with the present application, disclose devices which represent substantial improvements over the prior art. A flow passage is provided within a housing and is connectable to a source of IV fluid and to a delivery tube terminating at an administration needle. In the metering apparatus, a metering pin is axially movable within the flow passage relative to a valve seat and defining a flow passageway and a variable area flow notch which are positionable relative to the valve seat to regulate flow from a full flow purge position to a flow blocking position. In the preferred embodiment, the positioning of the metering pin is accomplished by a cam engaging a portion of the metering pin which forms a cam follower. The cam is manually adjustable by a dial on the device to accomplish accurate, repeatable and continuous flow adjustment over a full range. The system incorporates the metering apparatus, source of IV fluid, drip chamber and administration means. This apparatus and system works particularly well providing a high degree of accuracy and is competitive even with electronic flow controllers.

The foregoing devices, particularly those described immediately above, provide substantial improvements over conventional pinch valve and roller clamps, nevertheless are not economically justifiable in some applications or for some medical facilities. Accordingly, there exists a need for a reliable, accurate and repeatable IV flow control device which is simple, effective, accurate and which can be provided to the medical care industry at low cost.

Briefly, the present invention achieves the above objects and advantages and provides a unique IV control device which can be adjusted to maintain various settings from zero to full flow with accuracy and repeatability.

In accordance with the preferred embodiment, the flow control device of the present invention comprises a housing of a first plastic material which has an inlet and outlet port. A flow metering member having a variable area flow passage is rotatable within the housing by means of a manually adjustable dial. The flow metering member selectively places the inlet and outlet port in communication via the flow passageway to regulate the flow from a purge position through a flow adjusting range and to a stop flow position. The housing inlet and outlet are connectable in the IV tubing line which attaches the source of IV fluid to the administration needle. The metering member is fabricated of a second plastic material which is selected to effect sealing and minimize heat shrinkage. In other aspects of the present invention, a housing or backplate member may be selectively attachable to the valving member to provide additional gripping surface for the medical attendant. A security cover may also be associated with the valving member to secure the valving member from tampering or inadvertant adjustment by unauthorized persons.

The above and other objects and advantages of the present invention will become more readily apparent from the following description, claims and drawings in which:

FIG. 1 is a perspective view of the metering device of the present invention;

FIG. 2 is an exploded view of the metering device shown in FIG. 1;

FIG. 3 is a sectional view taken along lines 3—3 of FIG. 1;

FIG. 4 is a plan view of the metering face of the rotary metering member;

FIG. 5 is a sectional view taken along lines 5—5 of FIG. 4 showing the metering groove in a linear display;

FIG. 6 is a partial detail view showing the relationship of the metering member and the inlet and outlet;

FIGS. 7A to 7C are plan views of the metering member illustrating various positions thereof;

FIG. 8 is an exploded view of an alternate embodiment of the present invention;

FIG. 9 is a sectional view taken along lines 9—9 of FIG. 8;

FIGS. 10, 11 and 12 are partial sectional views as indicated in FIG. 9;

FIG. 13 is an exploded view of another embodiment of the present invention;

FIG. 14 is a sectional view taken along lines 14—14 of FIG. 13;

FIG. 15 is a rear perspective view of the embodiment of the invention shown in FIGS. 13;

FIG. 16 is a perspective view of a detachable backplate;

FIG. 21 is a perspective view of a valve assembly including an optional backplate and cover;

FIG. 22 is an exploded perspective view of the assembly shown in FIG. 21;

FIG. 23 is a perspective view similar to FIG. 21 with the cover plate removed;

FIG. 24 is a sectional view;

FIG. 25 is a rear exploded view of the flow control valve and connecting tubing;

FIG. 26 is a perspective view similar to FIG. 21 with the cover in an open position;

FIG. 27 is an exploded view of another embodiment of the metering valve; and

FIG. 28 is a sectional view of the valve of FIG. 27.

Figure 17:
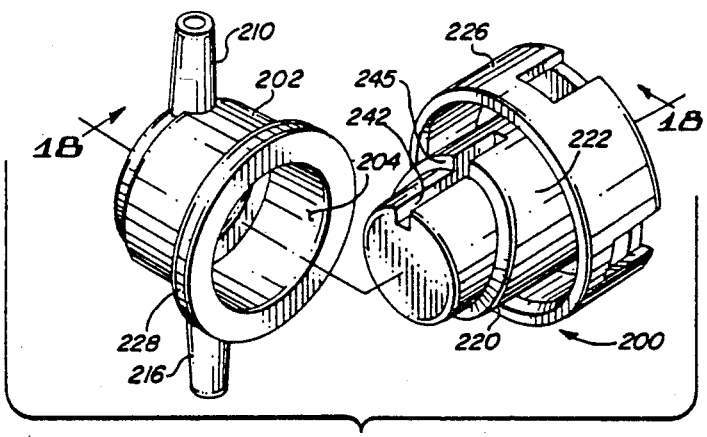
FIG. 17 is an exploded perspective view of another embodiment of the present invention.

Turning now to the drawings, FIGS. 1 and 2 generally show an embodiment of the flow control device of the present invention which is designated by the numeral 10. Valve 10 includes a generally planar rear wall 12 to which is secured an annular body member 14 which define a cylindrical valving chamber 16. Wall 12 may be configured in any desired shape for convenience but preferably extends laterally and longitudinally beyond the annular housing member 14 to provide a surface which can be easily accomodated and gripped by the user when adjusting the valve. In the simplest form, the marginal portion of the rear wall 12 extending beyond the annular housing 14 could be eliminated so the external valve body would be cylindrical.

Inlet fitting 20 and outlet fitting 22 extend from the rear of backplate 12 and are adapted to be connected to conventional I.V. tubing which, respectively, connect to a container of an appropriate IV solution and to the administration needle, not shown. Inlet fitting 20 communicates with metering chamber 60 through port 24. Similarly, fitting 22 communicates with the metering chamber 16 through outlet port 26. Ports 24 and 26 are shown as being diametrically opposed in the valve chamber 16. A small projection 30 is provided at the intersection of the backplate in the interior of housing member 14 to serve as a stop. The rear wall, inlet and outlet connections and housing are formed as an integral member preferably by injection molding and are preferably selected from a plastic material which is moldable, rigid, hard, heat resistant, medically acceptable, chemically inert, sterilizable and which will hold tolerance even under high temperatures. Typical of these classes of plastics are ABS, XT Polymer as manufactured by Cyro Industries and polycarbonate. A particular critical requirement is that the material must not flow or deform under hoop stress. Other similar materials exhibiting these characteristics are known to those in the plastic arts.

Circular gasket 32 having a diameter adapted to be received within the rear of chamber 16 which is provided and occupies a position immediately adjacent the rear wall 12. The gasket has a notch 34 which cooperates with projection 30 to keep the gasket in position and to prevent it from rotating within the chamber 16. Circular port 35 aligns with port 24 in the backplate and port 36 aligns with port 26 in the backplate to allow flow of fluid across the gasket. Preferably the gasket is of a plastic material which is softer than that of the housing. Preferably the housing and gasket should have a Shore hardness differential. Typically one component would be on the Shore A scale and the other on the Shore D scale. In addition, the gasket must not appreciably shrink when exposed to higher temperatures up to 165° F. and must not permanently deform under pressure and must retain its resiliency and memory. In this way, a seal is effected at the face of the gasket which eliminates or at least reduces the requirements for additional sealing members. Typically, gasket 32 would be formed from a material such as silicone, silicone rubber, Neoprene, C-flex, Krayton manufactured by Shell Chemical, Gaflex, LDP or plasticized PVC.

Rotary flow control member 40 is provided with a generally cylindrical hub 42 having a valving face 44. The hub is receivable within valving chamber 16. In the assembled position, the valving face 44 engages the outer face of gasket 32. A central axle 48 is received within opening 50 axially positioned within the metering hub 16 and aligned with hole 52 in gasket 32 to facilitate rotation of member 40. A dial 54 is secured to the outer surface of the rotary member 40 and is preferably provided with projections 56 to accomodate firm gripping by the user. The user can conveniently rotate the valving member relative to the valve body. The dial 56 extends beyond the edge of the housing 14 to facilitate rotation of the rotary flow control member.

The valving function is accomplished at valving face 44. Valving face 44 is provided with an arcuate groove 60 which extends for approximately 330° to 350°. A land area 62 is provided intermediate the opposite ends 64 and 65 of the groove and when the land 62 aligns with the inlet port 34 in gasket 32, the metering valve is in the off position as flow is blocked, as seen in FIG. 7A. Metering groove 60 is constructed having an area of approximately 180° in regime A of substantially uniform depth. Regime B which extends the remainder of the length of the groove is of varying cross-section diminishing in area as land 62 is approached toward end 65. Regime B may be of various cross-sectional configurations diminishing in cross-sectional area as the land is approached to provide a decreasing flow path and providing increasing resistance to flow as the area decreases.

Valving member 40 may be rotated by means of dial 54 to place inlet port 24 and outlet port 26 in communication via regime A of the metering groove. In this position, the valve is in the full flow or purge position. As seen in FIG. 7C, flow through the device is directed through the flow passage in Regime A which is of substantially uniform cross-section and provides a full flow or purging condition which is generally used to void the system of air.

The metering portion of Regime B of the metering groove may be of various cross-sectional configurations and is shown as being of generally uniform width but having decreasing depth. The metering portion of Regime B may also be of uniform depth and have a decreasing width or in some cases may decrease in both width and depth. It is also possible to reverse the orientation of the flow passage and the metering notch, as illustrated in FIG. 7B. With the flow directed from inlet port 24 through part of Regime B to the outlet port 26, metering is achieved and as the metering member is rotated counter-clockwise as seen in FIG. 1, flow is decreased continually and with precise regulation throughout the flow range.

The advantages of the metering valve of the type described above is that it is accurate, repeatable and is simple to operate. The use of selected plastic materials of different groups, one for the moveable member and the other for the housing or sealing member, achieves economy and also increases the reliability of the valve as the materials serve to seal the valve so that the requirement for additional O-rings or other sealing devices between the relatively moving parts in minimized.

Leakage is a problem in such valves and is of two types. External leakage in which fluid escapes from the unit and internal leakage which is contained but which may adversely effect the accuracy of the unit. A silicon fluid may be added to reduced frictional resistance to movement.

FIGS. 8 through 13 illustrate another embodiment of the present invention having a housing member 60 fabricated from a suitable rigid, hard plastic material as described above. The housing 60 includes a generally planar rear wall 62 with a generally cylindrical hub 64 thereon which defines a cylindrical valving chamber 65. An inlet fitting 68 and an outlet fitting 70 are positioned to communicate with the chamber 65 at diametrically opposed inlet and outlet ports 72 and 74.

Rotative metering member 80 includes a generally cylindrical hub 82 which is rotatably received within chamber 65 about axle 98 which is received in a recess at the rear of the chamber 65 in a tight fit. Preferably the rotative member is molded of a suitable relatively soft plastic material such as described above dissimilar from that of the housing 60 so that a suitable fluid-tight seal is formed between the relatively hard and soft plastic materials of the two components. The relative characteristics of the preferred materials of the housing and rotative member have been discussed above with regards to FIGS. 1 to 7 and a differential Shore hardness is requisite. The hub 80 is provided with a generally circular dial 84 which is serrated or provided with raised portions 86 for improved gripping characteristics.

Metering of flow between the inlet port 72 and outlet port 74 is accomplished via flow passage 90 which is formed in the surface of the cylindrical barrel or hub 82. As best seen in FIG. 9, the metering passage is formed having a regime or section A which is of substantially uniform cross-sectional area and which extends approximately 180° or more around the outlet cylindrical surface of the hub. The portion of the flow passage in regime B decreases in cross-sectional area having a maximum area at the intersection with regime A and diminishing to the point of termination 94. A land area 95 is provided intermediate the opposite ends of the flow passageway 90. As seen in FIGS. 10, 11 and 12, the flow passageway has the greatest cross-sectional area in the regime A and decreasing in cross-sectional area in regime B. Again, by rotating the dial member 80, the flow can be entirely blocked at inlet port 72 by registering land 95 with port 72 and flow can be varied from full flow or purge to a reduced rate continuously over the flow range of the valve. The use of plastic materials having dissimilar hardness and other characteristics for the housing and rotative valving member provides better sealing against fluid leakage out of the metering flow passageway and maintains exact, non-bypassing and constant fluid volumes to be contained totally within the passageway with no false fluid delivery via bypassed seepage.

In FIGS. 13 through 16, another embodiment of the present invention is shown which is generally designated by the numeral 100 and again includes a valve body member 102 having an inlet 104 and outlet 106 communicating with a flow chamber 108 defined by generally cylindrical body member 110. Again, the body member is fabricated preferably by injection molding from a selected plastic that is relatively hard as has been described above.

A generally annular, elastomeric sealing member 112 is positioned within hub 110. Member 112 is formed of a softer plastic material than is rotatable metering member 125. For example, sealing member 112 typically would be selected from the group of softer material described above whereas members 100 and 125 would be fabricated from the rigid, hard materials as described. Member 112 has oppositely disposed ports 114 and 116 which register with inlet 104 and outlet 106 respectively. Projection 118 on the interior of housing 110 cooperates with a notch 120 in the elastomeric member to prevent it from turning and twisting and to insure proper registry within the valve housing.

Rotatable valving member 125 includes a hub 128 which is rotatably received within elastomeric sealing member 112. Member 125 is secured in place at bore 129 in the rear of the valving member by axle 130 which has a tapered head 131 which compresses to allow it to be inserted through hole 129 and thereafter expands to secure member 125 in place. A circular dial 132 is positioned at the face of the unit and provides a surface for gripping by the user for manipulation and attendant adjustment of the flow rate.

As seen in FIG. 14, a valving passageway 140 is provided in the annular surface of the hub having a land area 128 intermediate the opposite ends of the passageway. The passageway is generally configured as has been described with reference to FIGS. 8 through 12 having a purge and flow metering region so additional detailed desc170 not deemed necessary. It will be apparent that as the hub 125 is rotated by means of dial 132 relative to the inlet 104 and outlet 106, valving will be accomplished from a stop position through full flow and metering.

As seen in FIG. 15, the rear surface 142 of valve body 102 is provided with a pair of diametrically opposed lugs 145 which extend outward from surface 142. Each of the lugs 145 has a radially extending wing or projection 147. Lugs 145 are integrally formed with the valve housing.

In the event the user requires additional gripping surface for holding the valve body when making adjustments to the flow rate, the optional backplate 150 as shown in FIG. 16 may be attached to the rear of the valve body. The backplate 150 consists of an elongate panel 152 having a width generally corresponding to the width of the body of valve 102 and having sufficient length to extend at least to or beyond the termination of the inlet and outlet ports 104 and 106. The opposite sides of body 150 are provided with forwardly extending flanges 156 and 158 which provide a further gripping surface to facilitate manipulation of the valve. A pair of bayonnet slots 160 and 162 are defined in the opposite sides of the valve body adapted to receive lugs 145. To secure the backplate 150, lugs 145 are inserted in the wide portion of the bayonnet slots and the valve body is the rotated, locking the valve body to the valve plate. Apertures 168 and 169 may be provided at opposite ends of the backplate so the backplate and the valve can be secured to appropriate locations such as an IV stand.

Figure 18:
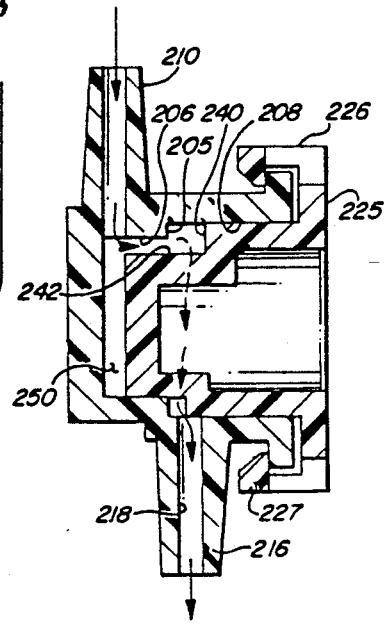
FIG. 18 is a sectional view taken along lines 18—18 of FIG. 17.
Figure 18A:
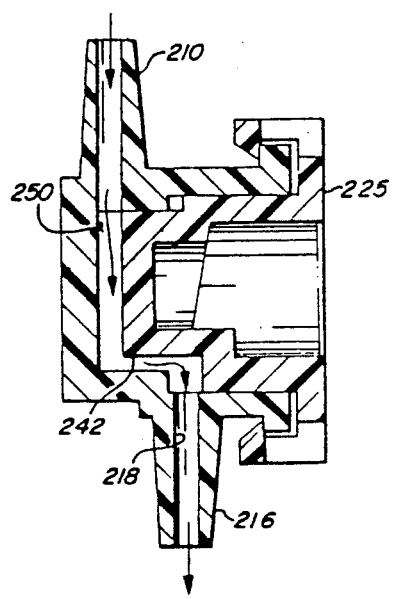
FIG. 18A is a view similar to FIG. 18 showing the valve of this embodiment in a purge position.

Another embodiment of the IV valve of the present invention is shown in FIGS. 17, 18 and 18A and is generally designated by the numeral 200. In this embodiment, the valve includes a body member 202 which is generally cylindrical defining a valving chamber 204 which is stepped having a shoulder 205 forming a smaller diameter section 206 at the rear of the chamber and a larger section 208 at the open end of the chamber. Fitting 210 defines an inlet port 212 which communicates at the rear of the valve chamber with the smaller diameter section 206. Fitting 216 defines a port 218 which communicates with the larger diameter section 208 of the chamber is the area adjacent shoulder 202. As best seen in FIG. 17, the inlet and outlet are positioned approximately 180° apart diametrically opposed on the housing.

The rotary valve member 220 has a body which has a large diameter inner cylindrical section 222 and a smaller diameter cylindrical section 224 which form an interference fit within the valve chamber 204 but permits rotation of the valve member. A dial surface 225 is provided on the outer face of valve body having an annular flanged skirt 226 with an inwardly turned lip 227 which engages a peripheral flange 228 on the valve body 202. As best seen in FIGS. 18 and 18A, lip 227 serves to secure the valve body in position to prevent separation of the assembled valve. The flange may be also cooperate with a projection on the valve body to serve as a stop or limit as to rotation in either direction.

Preferably the valve body is a rigid, hard plastic material such as ABS, XT or the like which has the characteristics of being able to be bonded by solvents. The valve body member 220 preferably is a semi-rigid material such as PVC, LDP, C-Flex or other similar materials known to those of the art which accomodate tolerance variations and will maintain the proper seal with the rigid material of the body. The characteristics of the preferred materials has been set forth above.

The valving function is accomodated by means of a helical ramp 240 formed in the outer surface of the rotary valve member 220. An axially extending groove 242 is provided in the outer surface of the valve body member. The keyway-like groove 242 is molded into the valve body and extends axially past ramp 240 intersecting the larger diameter portion 244 of the rotary valve member. A small section of helical ramp 240 forms a land 245 immediately adjacent the groove 244 which remains in contact with shoulder 202 of the valve body. The remainder of the ramp portion is in the form of a helix which is ramped towards the open end of the rotary valve member and intersects the groove 242 at the other end, as best seen in FIG. 17.

In operation, the valve 200 is in the full open or purge position as seen in FIG. 18A when the groove 242 is aligned with the lower port 218. In this position, fluid will flow through the inlet port 212 and down along the chamber is space 250 at the rear of the valve and through groove 242 to outlet 218. When the rotary valve member is rotated to a flow metering position, IV fluid will flow from the inlet through the passageway defined by should 202 and helical ramp 220 to the outlet port 218. As the valve body member is further rotated, the reduced size of the flow passageway and increased flow passage length will effect flow metering. When groove 242 is positioned at about four o'clock, the land 245 will block the channel creating a full off position.

The advantages of embodiment 200 are that the construction is simple and may be manufactured by plastic molding techniques. The construction utilizing a rigid, hard plastic housing and a softer material for the rotary valve member eliminates the need for expensive and complex seal arrangement between the body parts. The valve provides a full range of flow regulation throughout the rotation of the valving member.

Figure 19:
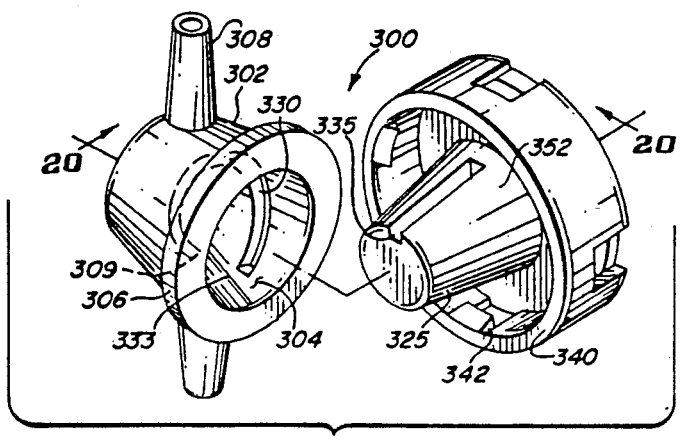
FIG. 19 is an exploded perspective view of still another embodiment of the flow control device of the present invention.
Figures 20, 20A:
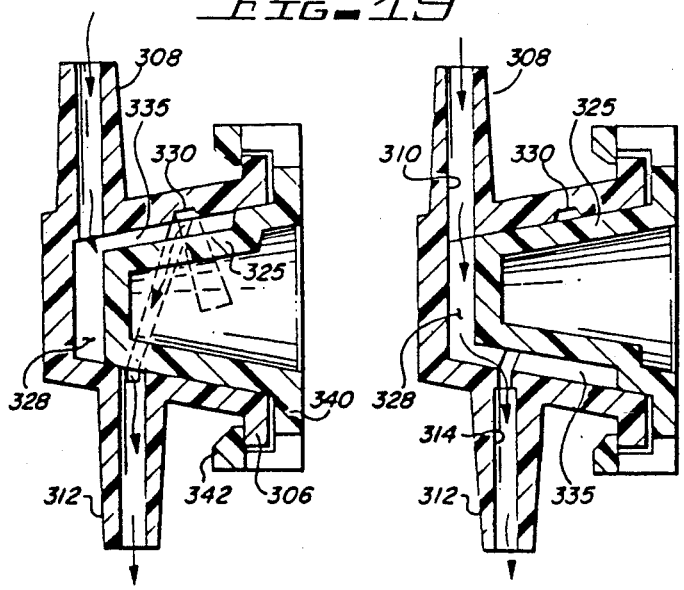
FIGS. 20 and 20A are sectional views taken along lines 20—20 of FIG. 19 showing the flow control valve in two different positions.

Still another embodiment of the present invention is shown in FIGS. 19 and 20 and is generally designated by the numeral 300. In embodiment 300 a valve body 302 is provided having a generally frustroconical valve chamber 304. A peripheral flange 306 is provided at the opening to valve chamber 304 which cooperates in locking fashion with flange 340 and projection 342 on the valve body. Inlet fitting 308 defines an inlet port 310 which communicates with the valve chamber 304 at the rear of the valve. An outlet fitting 312 defines outlet port 314 which communicates with the valve chamber 304 at an intermediate position.

Valving is accomplished through rotation of valving member 322 which is provided with internal body member 325 which is generally frustroconical and tightly engages the valve chamber 304. Valve body 325 terminates at a location spaced from the rear wall of chamber 304 so a passageway 328 is provided at the rear of the valve chamber.

A valving passageway 330 is provided on the interior surface of the valve body 302. Passageway 330 starts approximately at the intersection of the outlet port 314 with chamber 304 and proceeds in helical fashion around the interior of the chamber 304 for approximately 300°. The passageway 330 has its maximum cross-sectional area at its intersection with the outlet port and diminishes in cross-sectional area to its termination point 309. The passageway may be provided a taper at one or both side walls or the bottom wall of the groove may decrease in depth proceeding along the groove. An axial slot 335 is provided in the outer surface of the frustroconical rotary valve body to establish a full-flow or purge position.

The full open or purge position is provided when the groove 335 is in the six o'clock position communicating with outlet port 314, as seen in FIG. 20A. It will be apparent from FIG. 20A that fluid will flow through the inlet port 310, along passageway 328 and through groove 335 to outlet port 314. Rotating the valve member 322 in a clockwise position causes the groove 335 to communicate with the more shallow portion of the helical passageway 330 to regulate flow. The portion 333 of frustroconical chamber 304 devoid of the passageway 330 provides a full off position when in registry with the outlet port 314, as shown in FIG. 20.

The construction of this embodiment provides a simple and effective valving member providing a purge position, full off and infinite adjustability throughout the metering range. The construction of the valve allows the valve components to be molded of plastic preferably with the valve body of a softer semi-rigid material and the other component being made of a rigid material to achieve sealing. As mentioned above, the rigid material may be ABS or XT or the like with the other component made from LDP, PVC or similar materials well-known to those in the plastic molding arts.

FIGS. 21 through 26 show still another embodiment of the present invention which is generally designated by the numeral 500. In this embodiment, the basic flow control device is provided with several accessories which may be included at the option of the user. The embodiment of these figures includes the basic metering valve designated by the number 502 which may be in the form of any of the valves heretofore described having a rotary dial member 504 for adjusting flow through the valve housing 505 and having inlet and outlet fittings 506 and 508 respectively. The basic valve 502 is an in-line valve adapted to regulate IV fluid flow from full flow to an off position with infinite variation between these positions by selective positioning of the variable area flow passageway 509.

The valve 502 is compact and is designed to be manually operated and in some applications its size and weight are an advantage as for example in an extension IV set where the light-weight would exert little pull on the needle at the venapuncture site. However, in some other instances, it is desirable that the valve lend itself to one-hand operation. This allows the medical attendant to adjust the valve with one hand while performing other operations with the other hand. To this end, an optional backplate providing additional area for the user to grasp may be provided. The backplate of this embodiment is generally designated by the numeral 510 and can be molded as a one-piece unit from a suitable plastic material. The backplate includes a generally planar rear surface 512 and opposite forwardly extending side edges 514 and 516. The side edges are generally parallel and are spaced apart a distance less than the diameter of the body of valve 502. The side edges 514 and 516 both diverge outwardly at an intermediate location having a curvature generally corresponding to the curvature of the circular housing of the valve member 502 to form a receptacle 515 for housing 505 of the metering valve. In this way, valve 502 can be positioned in the backplate 510 and secured by an interference-fit with the valve body. Projections 525 extend in the receptacle 515 to engage the body 505 of the valve when inserted into the backplate. Note that in the assembled position, the diameter of the dial 504 exceeds the width of the backplate so that the operator can conveniently grasp the unit with the backplate resting in the palm of the hand and use the thumb and forefinger to grasp the dial from the rear to make the necessary adjustment.

The opposite ends of the backplate are recessed at 520 and 522 to accomodate the incoming and outgoing IV fluid lines 521 and 523. An upwardly extending projection 530 is provided at the upper left hand edge of the backplate as viewed in FIGS. 21 and 22. Projection 530 serves as part of a release mechanism when the valve is used with a cover as explained below. The lower opposite sides 514 and 516 are provided with apertures 532 and 534 to accomodate a cover if desired.

The cover which may be optionally attached to the backplate is generally designated by the numeral 550. The cover may be oppositely attached when it is desired to provide additional security to prevent either intentional or inadvertent adjustment of the setting of the valve as, for example, in the case of juvenile patients. The cover 550 includes a generally flat cover plate 552 having opposite depending sides 554 and 556. A portion of the cover is configured as a generally cylindrical receptacle 560 adapted to receive the dial portion 504 of contained valve 502. The lower end of opposite sides 554 and 556 depend below the cover plate 552 and are provided with inwardly extending pins or axles 562 which are receivable within holes 532 and 534 at the opposite sides of the backplate. Since the device is preferably made of a suitable flexible plastic, sides 554 and 556 can be deflected outwardly a sufficient distance to engage the in the cooperating holes 532 and 534. Thus, when assembled, the cover is pivotally attached to the backplate and may be positioned in an open position as shown in FIG. 26 or pivoted upwardly to a closed position as shown in FIG. 21. Latch members 558 and 560 at the interior of the sides 554 and 556, engage the edge of the back cover to secure the cover in a closed position. Projection 575 extends upwardly from the upper right hand edge of the front cover as seen in FIG. 26. Thus, to open the cover, projection 530 on the backplate and projection 575 on the cover plate may be easily forced in opposite directions to unlock the cover. A cut-out 580 is provided in the face of the cover so that the attendant can visually determine the setting of the valve. Alternatively, the backplate and cover may be molded as one piece and incorporate a connecting "live" hinge of a thin plastic membrane that allows opening and closing of the security cover.

In FIGS. 27 and 28, an alternate configuration for the valve is illustrated. Here the valve body 602 is generally cylindrical defining a valving chamber 604 having an inlet and an outlet 606 and 608, respectively. Annular flange 610 extends about valve body to receive rotary valve member 615. The rotary valve member includes a barrel 618 having a variable area metering slot 620 formed in the wall which is rotatable to regulate flow. The barrel 618 is preferably of a softer plastic material than housing body 602 for better sealing and is further selected to resist shrinkage. Barrel or body 618 has a concentric bone 626 with keyway 628 to receive axle 630 of the separate dial assembly 632. The dial 632 is of a more rigid plastic material and is locked in the barrel against rotation by axial key 635 which is received in keyway 628. Annular locking member 640 with flanged section 642 engaged flange 610 to secure the assembly. The circular dial portion may have a beveled and serrated edge for better manual control.

Flange 610 has a vertically extending stop portion 650 which terminates at pointer 655. The rotation of the dial and associated barrell is limited as flange 642 will engage the stop 650. Thus, uni-directional operation can be achieved with increasing flow in one direction and decreasing in the other. Appropriate indicia may be placed on the face of dial 632 which is cooperable with pointer 655 to provide an indication of flow setting.

Thus, it will be seen from the foregoing that the basic valve as described herein can be economically manufactured and provide the accuracy and repeatability necessary. In addition, the valve can further be provided with a backplate as an accessory to enhance the operation of the device and to make it compatible with one-hand operation. If security is desired, the optional cover plate can be attached to the backplate. Thus, in its simplest and economical form, the valve alone can be used in IV administration. For other applications, the medical attendant can add either the backplate or the backplate and the cover plate as required and dictated by the particular application and procedure.

The unique design and construction of the valving components avoids complex sealing arrangement and are economical to fabricate so the unit can be provided to health care facilities as an inexpensive, disposable item. This unit resists tampering and is accurate and simple for the medical attendants to operate giving accurate, repeatable results.

It will be obvious to those skilled in the art to make various changes, alterations and modifications to the invention described herein. To the extent those changes, alterations and modifications do not depart from the spirit and scope of the appended claims, they are intended to be encompassed therein.

I claim:

1. A valve for establishing and maintaining predetermined administration flow rates in an IV system having a source of fluid connected to an administration needle via a flexible tubing line, said valve comprising:

(a) a valve housing of a first material defining a generally cylindrical valving chamber, said housing having an inlet and an outlet communicating with said valving chamber and connectable in said tubing line;

(b) a valving drum having a generally cylindrical outer surface and defining a centrally extending recess, said drum defining a flow path along its outer surface and being rotatable in said chamber to selectively position said flow path to vary the flow rate from the valve inlet to the outlet across said flow path, said drum being of a material which is relatively softer than the material of said housing;

(c) means for manually rotating said valving drum; and (d) projection means positioned within said recess and internally supporting at least a portion of said valving drum to maintain said drum outer surface and said valving chamber in sealing contact.

2. The valve of claim 1 wherein said valve housing, drum and projection means are plastic.

3. The valve of claim 1 wherein said flow path is configured to vary the flow rate from an off to a full-flow rate with variable flow therebetween.

4. The valve of claim 1 wherein said means for manually rotating said valving drum comprises dial means exterior of said housing.

5. The valve of claim 4 further including indicia means on said dial means.

6. The valve of claim 4 wherein said dial means are integral with said projection means.

7. The valve of claim 1 wherein said drum has a substantially flat interior end and said recess extends concentrically within said drum to said interior end wall.

8. The valve of claim 1 wherein said valve housing and drum are molded plastic.

* * * * *